United States Patent [19]

Fischer, deceased

[11] 3,963,474
[45] June 15, 1976

[54] HERBICIDE MIXTURES OF 3-LOWER ALKYL-2,1,3-BENZOTHIADIAZINONE-(4)-2,2-DIOXIDES OR SALTS THEREOF AND 2-(METHYL, CHLOROPHENOXY)-N-METHOXYACETAMIDES

[75] Inventor: Adolf Fischer, deceased, late of Mutterstadt, Germany, by Caecilia Emma Fischer, legal representative

[73] Assignee: BASF Aktiengesellschaft, Ludwigshafen (Rhine), Germany

[22] Filed: Feb. 10, 1975

[21] Appl. No.: 548,387

Related U.S. Application Data

[62] Division of Ser. No. 432,675, Jan. 11, 1974, abandoned, which is a division of Ser. No. 343,629, March 22, 1973, Pat. No. 3,888,655.

[30] Foreign Application Priority Data
Apr. 13, 1972 Germany............................ 2217722

[52] U.S. Cl.................................... 71/91; 71/118
[51] Int. Cl.².......................................... A01N 9/12
[58] Field of Search................................ 71/91, 118

[56] References Cited
UNITED STATES PATENTS 3,168,561  2/1965  Richter................................ 71/118
3,473,913  10/1969  Zick...................................... 71/118
3,708,277  1/1973  Zeidler et al........................... 71/91

OTHER PUBLICATIONS

Fischer I, "Herbicidal Compositions" (1971) CA 74 No. 110714w, (1971).
Fischer II, "Herbicidal Compositions, etc.," (1971) CA 75, No. 75217h, (1971).

*Primary Examiner*—Glennon H. Hollrah
*Attorney, Agent, or Firm*—Johnston, Keil, Thompson & Shurtleff

[57] ABSTRACT

Herbicide compositions of mixtures in the weight ratio of 5:1 to 1:5 of (a) 3-lower alkyl-2,1,3-benzothiadiazinone-(4)-2,2-dioxide or a salt thereof and (b) a compound of the formula

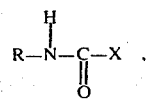

where R denotes methoxy and X denotes phenoxymethyl bearing halogen and methyl substituents in the phenyl radical.

10 Claims, No Drawings

HERBICIDE MIXTURES OF 3-LOWER ALKYL-2,1,3-BENZOTHIADIAZINONE-(4)-2,2-DIOXIDES OR SALTS THEREOF AND 2-(METHYL, CHLOROPHENOXY)-N-METHOXYACETAMIDES

RELATED APPLICATION

This application is a division of my copending application Ser. No. 432,675, filed Jan. 11, 1974, now abandoned which in turn is a division of my application Ser. No. 343,629, filed March 22, 1973, now U.S. Pat. No. 3,888,655 the disclosures of which are incorporated herein by reference.

The present invention relates to a herbicide comprising a composition of several active ingredients.

It is known that substituted phenyl ethers, carbamates, terephthalates, acid amides, benzoic acids, fluorenecarboxylic acids and benzothiadiazinones have a herbicidal action. However, this action is poor.

I have now found that a composition of
a. a compound of the formula

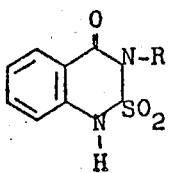

where R denotes lower alkyl of a maximum of 4 carbon atoms, or its salts, such as alkali metal, alkaline earth metal, ammonium, hydroxyalkylammonium, alkylammonium and hydrazine salts, e.g. salts with sodium, lithium, potassium, calcium, iron, methylammonium, trimethylammonium, ethylammonium, diethanolammonium, ethanolammonium, dimethylamine, dimethylethanolamine, hydrazine and phenylhydrazine, and b. a compound of the formula

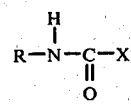

where R denotes methoxy, alkynyl of 5 carbon atoms or a 5-chloro-4-methylthiazolyl radical and X denotes phenoxymethyl bearing halogen and methyl substituents in the phenyl radical, dichlorophenyl, or lower alkyl. have a herbicidal action superior to that of their individual components.

Active ingredients a and b may be applied in amounts of 0.5 to 5 kg per hectare.

The weight ratio of $a : b$ is from 5:1 to 1:5, preferably from 3:1 to 1:3.

The compositions of the invention are suitable for controlling unwanted plants, e.g. dicotyledonous seed weeds, monocotyledonous grassy seed weeds and Cyperaceae in crops such as cereals, rice, soybeans, Indian corn, potatoes, peas, and beans.

The compositions may be applied to the loci of the plants, pre- and/or postemergence.

The agents according to the invention may be used as solutions, emulsions, suspensions oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

EXAMPLE 1

The plants rice (*Oryza sativa*), soybeans (*Soja hispida*), Indian corn (*Zea mays*), wheat (*Triticum aestivum*), barnyard grass (*Echinochloa crus-galli*), giant foxtail (*Sertaria faberii*), yellow nutsedge (*Cyperus esculentus*), common cocklebur (*Xanthium pensylvanicum*), wild mustard (*Sinapis arvensis*), waterplantain (*Alisma plantago-aquatica*), catchweed bedstraw (*Galium aparine*), chamomile (*Matricaria chamomilla*), slender foxtail (*Alopecurus myosuroides*) and annual bluegrass (*Poa annua*) were treated at a growth height of 4 to 20 cm with the following individual active ingredients and compositions thereof, each active ingredient and each composition being emulsified or dispersed in 500 liters of water per hectare:

I 2,4'-dinitro-4-trifluoromethyldiphenyl ether, 1.5 and 3 kg per hectare;
II 4'-nitro-2,4,6-trichlorodiphenyl ether, 2 and 3 kg per hectare;
III N-(1,1-dimethylpropynyl)-3,5-dichlorobenzamide, 1 and 3 kg per hectare;
IV 2-(2-methyl-4-chlorophenoxy)-N-methoxyacetamide, 1 and 2 kg per hectare;
V 2,3,6-trichlorobenzoic acid, 0.5 and 2 kg per hectare,
VI 2-methoxy-3,6-dichlorobenzoic acid, 1.5 and 2 kg per hectare;
VII 3-isopropyl-2,1,3-benzthiadiazinone-(4)-2,2-dioxide, 0.5, 1, 1.5, 2 and 3 kg per hectare;
I + VII: 1.5 + 1.5 kg per hectare;
II + VII: 2 + 1 kg per hectare;
III + VII: 1 + 2 kg per hectare;
IV + VII: 1 + 1 kg per hectare;
V + VII: 0.5 + 1.5 kg per hectare;
VI + VII: 1.5 + 0.5 kg per hectare.

After 8 to 14 days it was ascertained that the compositions had a better overall action than the individual active ingredients, combined with good crop plant compatability. The results are given below:

| Active ingredient kg/ha | I 1.5 | I 3 | II 2 | II 3 | III 1 | III 3 | IV 1 | IV 2 | V 0.5 | V 2 | VI 1.5 | VI 2 | VIII 0.5 | VIII 1 | VIII 1.5 | VIII 2 | VIII 3 |
|---|---|---|---|---|---|---|---|---|---|---|---|---|---|---|---|---|---|
| Oryza sativa | 10 | 25 | 10 | 20 | — | — | — | — | — | — | — | — | 0 | 0 | 0 | 0 | 0 |
| Soja hispida | 10 | 25 | — | — | 5 | 25 | — | — | — | — | — | — | 0 | 0 | 0 | 5 | 10 |
| Zea mays | — | — | — | — | — | — | 0 | 20 | — | — | — | — | 0 | 0 | 0 | 0 | 0 |
| Triticum aestivum | — | — | — | — | — | — | — | — | 0 | 20 | 10 | 15 | 0 | 0 | 0 | 0 | 0 |
| Echinochloa crus-galli | 65 | 95 | 60 | 90 | 40 | 80 | 40 | 70 | — | — | — | — | 0 | 5 | 5 | 10 | 10 |
| Setaria faberii | 65 | 90 | 60 | 90 | 35 | 70 | 45 | 75 | — | — | — | — | 0 | 5 | 5 | 10 | 15 |
| Cyperus esculentus | 45 | 80 | 30 | 55 | 20 | 55 | 5 | 10 | — | — | — | — | 20 | 36 | 45 | 65 | 90 |
| Xanthium pensylvanicum | 30 | 65 | 30 | 45 | 25 | 60 | 30 | 55 | — | — | — | — | 30 | 40 | 60 | 70 | 95 |
| Sinapis arvensis | 60 | 95 | 40 | 60 | 60 | 95 | 45 | 90 | — | — | — | — | 45 | 60 | 75 | 95 | 100 |
| Alisma plantago-aquatica | 30 | 50 | 15 | 30 | 20 | 55 | 20 | 45 | — | — | — | — | 20 | 40 | 60 | 75 | 80 |
| Galium aparine | — | — | — | — | — | — | — | — | 25 | 85 | 60 | 85 | 30 | 40 | 60 | 70 | 80 |
| Matricari chamomilla | — | — | — | — | — | — | — | — | 30 | 95 | 65 | 90 | 35 | 50 | 60 | 90 | 95 |
| Alopecurus myosuroides | — | — | — | — | — | — | — | — | 50 | 95 | 45 | 80 | 5 | 5 | 15 | 10 | 15 |
| Poa annua | — | — | — | — | — | — | — | — | 55 | 100 | 60 | 95 | 5 | 5 | 5 | 5 | 10 |

0 = no damage
100 complete destruction

| Active ingredient kg/ha | I + VII 2.5 + 1.5 | II + VII 2 + 1 | III + VII 1 + 2 | IV + VII 1 + 1 | V + VII 0.5 + 1.5 | VI + VII 1.5 + 0.5 |
|---|---|---|---|---|---|---|
| Oryza sativa | 10 | 10 | — | — | — | — |
| Soja hispida | 10 | — | 5 | — | — | — |
| Zea mays | — | — | — | 0 | — | — |
| Triticum aestivum | — | — | — | — | 0 | 10 |
| Echinochloa crus-galli | 90 | 90 | 80 | 70 | — | — |
| Setaria faberii | 90 | 85 | 75 | 75 | — | — |
| Cyperus esculentus | 100 | 95 | 100 | 100 | — | — |
| Xanthium pensylvanicum | 100 | 100 | 100 | 100 | — | — |
| Sinapis arvensis | 100 | 100 | 100 | 100 | — | — |
| Alisma plantago-aquatica | 100 | 90 | 100 | 100 | — | — |
| Galium aparine | — | — | — | — | 100 | 95 |
| Matricaria chamomilla | — | — | — | — | 100 | 95 |
| Alopecurus myosuroides | — | — | — | — | 80 | 75 |
| Poa annua | — | — | — | — | 80 | 80 |

0 = no damage
100 = complete destruction

EXAMPLE 2

In the greenhouse, various plants were treated at a height of from 2 to 20 cm with the following amounts of the following individual active ingredients and compositions thereof as aqueous solutions, emulsions, dispersions or suspensions:

I  3-isopropyl-2,1,3-benzothiadiazinone-(4)-2,2-dioxide, 1.5, 2, 2.5 and 3 kg/ha;

II  3-isopropyl-2,1,3-benzothiadiazinone-(4)-2,2-dioxide, sodium salt, 1.5, 2, 2.5 and 3 kg/ha;

III  3-isopropyl-2,1,3-benzothiadiazinone-(4)-2,2-dioxide, dimethylamine salt, 1.5, 2, 2.5 and 3 kg/ha;

IV  3-isopropyl-2,1,3-benzothiadiazinone-(4)-2,2-dioxide, diethanolamine salt, 1.5, 2, 2.5 and 3 kg/ha;

V  N-(1,1-dimethylpropynyl)-3,5-dichlorobenzamide, 0.5, 1 and 3 kg/ha;

VI  2-(2-methyl-4-chlorophenoxy)-N-methoxyacetamide, 0.5, 1, 1.5 and 3 kg/ha;

I + V, II + V, III + V and IV + V each at rates of 2.5 + 0.5 and 2 + 1 kg/ha;

I + VI, II + VI, III + VI and IV + VI each at rates of 2.5 + 0.5, 2 + 1 and 1.5 + 1.5 kg/ha.

After 2 to 3 weeks it was ascertained that the compositions had a better herbicidal action than their components, combined with the same crop plant compatibility.

The results are given below:

| Active ingredient kg/ha | I 1.5 2 2.5 3 | II 1.5 2 2.5 3 | III 1.5 2 2.5 3 | IV 1.5 2 2.5 3 | V 0.5 1 3 | VI 0.5 1 1.5 3 |
|---|---|---|---|---|---|---|
| Crop plants: | | | | | | |
| Glycine max | 0 0 5 10 | 0 0 5 15 | 0 0 7 12 | 0 0 5 10 | 0 5 25 | 0 5 15 35 |
| Zea mays | 0 0 0 0 | 0 0 0 0 | 0 0 0 0 | 0 0 0 0 | — — — | 0 0 10 30 |
| Oryza sativa | 0 0 0 0 | 0 0 0 0 | 0 0 0 0 | 0 0 0 0 | 0 10 40 | — — — |
| Unwanted plants: | | | | | | |
| Echinochloa crus-galli | 10 10 10 15 | 15 24 25 30 | 15 20 23 25 | 17 24 27 30 | 30 40 80 | 30 40 60 90 |
| Cyperus esculentus | 70 75 85 90 | 70 80 90 95 | 70 80 85 90 | 78 90 93 95 | 10 20 55 | 0 5 10 20 |
| Sinapis arvensis | 75 80 95 100 | 75 85 90 95 | 80 90 95 100 | 85 95 100 100 | 20 60 95 | 20 45 70 100 |

0 = no damage
100 = complete destruction

| Active ingredient kg/ha | I+V 2.5 2 0.5 1 | I+VI 2.5 2 1.5 0.5 1 1.5 | II+V 2.5 2 0.5 1 | II+VI 2.5 2 1.5 0.5 1 1.5 | III+V 2.5 2 0.5 1 | III+VI 2.5 2 1.5 0.5 1 1.5 | IV+V 2.5 2 0.5 1 | IV+VI 2.5 2 1.5 0.5 1 1.5 |
|---|---|---|---|---|---|---|---|---|
| Crop plants: | | | | | | | | |
| Glycine max | 5 5 | 5 5 15 | 5 5 | 5 5 5 | 7 5 | 7 5 15 | 5 5 | 5 5 15 |
| Zea mays | — — | 0 0 10 | — — | 0 0 10 | — — | 0 0 10 | — — | 0 0 10 |
| Oryza sativa | 0 10 | — — — | 0 10 | — — — | 0 10 | — — — | 0 10 | — — — |
| Unwanted plants: | | | | | | | | |
| Echinochloa crus-galli | 92 100 | 93 100 100 | 95 100 | 95 100 100 | 94 100 | 95 100 100 | 98 100 | 97 100 100 |
| Cyperus esculentus | 100 100 | 100 100 100 | 100 100 | 100 100 100 | 100 100 | 100 100 100 | 100 100 | 100 100 100 |
| Sinapis arvensis | 100 100 | 100 100 100 | 100 100 | 100 100 100 | 100 100 | 100 100 100 | 100 100 | 100 100 100 |

0 = no damage
100 = complete destruction

EXAMPLE 3

In the greenhouse, various plants were treated at a height of from 2 to 20 cm with the following amounts of the following individual active ingredients and compositions thereof as aqueous solutions, emulsions, dispersions or suspensions:

I   3-isopropyl-2,1,3-benzothiadiazinone-(4)-2,2-dioxide, 0.5, 0.75, 1 and 1.5 kg/ha;

II   3-isopropyl-2,1,3-benzothiadiazinone-(4)-2,2-dioxide, sodium salt, 0.5, 0.75, 1 and 1.5 kg/ha;

III   3-isopropyl-2,1,3-benzothiadiazinone-(4)-2,2-dioxide, dimethylamine salt, 0.5, 0.75, 1 and 1.5 kg/ha;

IV   3-isopropyl-2,1,3-benzothiadiazinone-(4)-2,2-dioxide, diethanolamine salt, 0.5, 0.75, 1 and 1.5 kg/ha;

V   N-(1,1-dimethylpropynyl)-3,5-dichlorobenzamide, 0.5, 0.75, 1 and 1.5 kg/ha;

VI   2-(2-methyl-4-chlorophenoxy)-N-methoxyacetamide, 0.5, 0.75, 1 and 1.5 kg/ha;

I + V, I + VI, II + V, II + VI, III + V, III + VI, IV + V and IV + VI each at rates of 0.5 + 1, 1 + 0.5 and 0.75 + 0.75 kg/ha.

After 2 to 3 weeks it was ascertained that the compositions had a better herbicidal action than their components, combined with the same crop plant compatibility.

The results are given below:

| Active ingredient kg/ha | I 0.5 0.75 1 1.5 | II 0.5 0.75 1 1.5 | III 0.5 0.75 1 1.5 | IV 0.5 0.75 1 1.5 |
|---|---|---|---|---|
| Crop plants: | | | | |
| Glycine max | 0 0 0 0 | 0 0 0 0 | 0 0 0 0 | 0 0 0 0 |
| Zea mays | 0 0 0 0 | 0 0 0 0 | 0 0 0 0 | 0 0 0 0 |
| Oryza sativa | 0 0 0 0 | 0 0 0 0 | 0 0 0 0 | 0 0 0 0 |
| Unwanted plants: | | | | |
| Echinochloa crus-galli | 4 7 10 10 | 2 8 10 15 | 5 9 10 15 | 7 10 12 17 |
| Cyperus esculentus | 20 40 60 70 | 20 30 45 70 | 20 35 50 70 | 25 30 53 78 |
| Sinapis arvensis | 30 45 60 75 | 25 40 50 75 | 30 40 55 80 | 30 42 62 85 |

0 = no damage
100 = complete destruction

| Active ingredient kg/ha | V 0.5 0.75 1 1.5 | VI 0.5 0.75 1 1.5 | I + V 0.5 1 0.75 1 0.5 0.75 | I + VI 0.5 1 0.75 1 0.5 0.75 |
|---|---|---|---|---|
| Crop plants: | | | | |
| Glycine max | 0 0 5 10 | 0 0 5 15 | 5 0 0 | 5 0 0 |
| Zea mays | — — — — | 0 0 0 10 | — — — | 0 0 0 |
| Oryza sativa | 0 5 10 25 | — — — — | 10 0 5 | — — — |
| Unwanted plants: | | | | |
| Echinochloa crus-galli | 30 35 40 70 | 30 35 40 60 | 80 75 80 | 70 65 68 |
| Cyperus esculentus | 10 15 20 30 | 0 2 5 10 | 80 100 97 | 72 98 87 |
| Sinapis arvensis | 20 40 60 80 | 20 30 45 70 | 100 100 100 | 100 100 100 |

0 = no damage
100 = complete destruction

| Active ingredient kg/ha | II + V 0.5 1 0.75 1 0.5 0.75 | II + VI 0.5 1 0.75 1 0.5 0.75 | III + V 0.5 1 0.75 1 0.5 0.75 | III + VI 0.5 1 0.75 1 0.5 0.75 | IV + V 0.5 1 0.75 1 0.5 0.75 | IV + VI 0.5 1 0.75 1 0.5 0.75 |
|---|---|---|---|---|---|---|
| Crop plants: | | | | | | |
| Glycine max | 5 0 0 | 5 0 0 | 5 0 0 | 5 0 0 | 5 0 0 | 5 0 0 |
| Zea mays | — — — | 0 0 0 | — — — | 0 0 0 | — — — | 0 0 0 |
| Oryza sativa | 10 0 5 | — — — | 10 0 5 | — — — | 10 0 5 | — — — |
| Unwanted plants: | | | | | | |
| Echinochloa crus-galli | 80 82 75 | 85 83 80 | 90 84 90 | 90 84 90 | 90 80 90 | 90 85 90 |
| Cyperus esculentus | 80 94 82 | 70 90 75 | 86 100 90 | 74 95 82 | 90 98 90 | 80 90 80 |
| Sinapis arvensis | 100 100 98 | 100 100 100 | 100 100 100 | 100 100 100 | 100 100 100 | 100 100 100 |

0 = no damage
100 = complete destruction

I claim:

1. A herbicide composition comprising an inert carrier having dispersed therein a herbicidally effective amount of a mixture consisting essentially of a. a compound of the formula

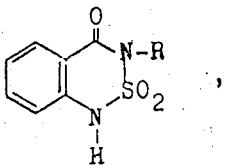

where R denotes lower alkyl of a maximum of 4 carbon atoms, or an alkali metal, alkaline earth metal, ammonium, lower alkylammonium, lower hyroxyalkylammonium, or hydrazine salt thereof, and b. a compound of the formula

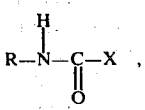

where R denotes methoxy and X denotes phenoxymethyl bearing chloro and methyl substitutents in the phenyl radical in a weight ratio of $a : b$ of 3:1 to 1:3.

2. A herbicide composition as claimed in claim 1 wherein compound (b) is 2-(2-methyl-4-chlorophenoxy)-N-methoxyacetamide.

3. A process for controlling growth of unwanted plants among crop plants which comprises applying to the locus of said plants a herbicidally effective amount of a herbicide composition containing a mixture consisting essentially of a. a compound of the formula

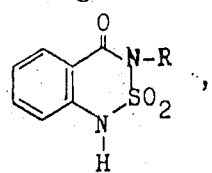

where R denotes lower alkyl of a maximum of 4 carbon atoms, or an alkali metal, alkaline earth metal, ammonium, lower alkylammonium, lower hydroxyalkylammonium, or hydrazine salt thereof, and b. a compound of the formula

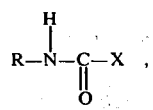

where R denotes methoxy and X denotes phenoxymethyl bearing chloro and methyl substituents in the phenyl radical in a weight ratio of $a : b$ of 3:1 to 1:3.

4. A process as claimed in claim 3 wherein compound (b) is 2-(2-methyl-4-chlorophenoxy)-N-methoxyacetamide.

5. A process as claimed in claim 4 wherein R in compound a is isopropyl.

6. A process as claimed in claim 4 wherein R in compound a is isopropyl, and said weight ratio is 1:1.

7. A process as claimed in claim 3 wherein R in compound a is isopropyl.

8. A herbicide composition as claimed in claim 1 wherein R in compound a is isopropyl.

9. A herbicide composition as claimed in claim 2 wherein R in compound a is isopropyl.

10. A herbicide composition as claimed in claim 2 wherein R in compound a is isopropyl, and said weight ratio is 1:1.

* * * * *